United States Patent [19]

Fields et al.

[11] Patent Number: 5,670,310
[45] Date of Patent: Sep. 23, 1997

[54] METHODS AND COMPOSITIONS FOR DIFFERENTIAL DIAGNOSIS OF ACUTE AND CHRONIC HEPATITIS C VIRUS INFECTION

[75] Inventors: Howard A. Fields, Marietta; Yury E. Khudyakov, Atlanta, both of Ga.

[73] Assignee: The United States of America as represented by the Department of Health and Human Services, Washington, D.C.

[21] Appl. No.: 282,758

[22] Filed: Jul. 29, 1994

[51] Int. Cl.⁶ .................... C12Q 1/70; G01N 33/576; C07K 7/08
[52] U.S. Cl. ........................... 435/5; 435/820; 530/326
[58] Field of Search ........................ 530/326, 329; 435/5, 820

[56] References Cited

U.S. PATENT DOCUMENTS 5,350,671  9/1994  Houghton et al. ................. 435/5

FOREIGN PATENT DOCUMENTS

| 0624 597 | 5/1994 | European Pat. Off. . |
| 4240980 | 2/1994 | Germany . |
| 2 051152 | 6/1994 | Spain . |
| WO93/06488 | 4/1993 | WIPO . |
| WO94/26932 | 11/1994 | WIPO . |

OTHER PUBLICATIONS

Saracco et al. "Hepatitis C virus markers in patients with long-term biochemical and histological remission of chronic hepatitis" *Liver* 14:65–70, 1994.

Bradley, et al., "Molecular characterization of hepatitis C and E viruses," *Arch. Virol.* 7:1–14 (1993).

Cerino and Mondelli, "Identification of an Immunodominant B Cell Epitope on the Hepatitis C Virus Nonstructural Region Defined by Human Monoclonal Antibodies," *The Journal of Immunology* 147:2692–2696 (Oct. 15, 1991).

Chien, et al., "Diagnosis of hepatitis C virus (HCV) infection using an immunodominant chimeric polyprotein to capture circulating antibodies: Reevaluation of the role of HCV in liver disease," *Proc. Natl. Acad. Sci. USA* 89:10011–10015 (Nov. 1992).

Kuo, et al., "An Assay for Circulating Antibodies to a Major Etiologic Virus of Human Non-A, Non-B Hepatitis," *Science* 244:362–364 (Apr. 1989).

Simmonds, et al., "Mapping of Serotype-Specific, Immunodominant Epitopes in the NS-4 Region of Hepatitis C Virus (HCV): Use of Type-Specific Peptides to Serologically Differentiate Infections with HCV Types 1, 2, and 3," *Journal of Clinical Microbiology* 31:1493–1503 (Jun. 1993).

Wong, et al., "Longitudinal Analysis of the Humoral Immune Response to Human Immunodeficiency Virus Type 1 (HIV-1) gp160 Epitopes in Rapidly Progressing and Nonprogressing HIV-1-Infected Subjects," *The Journal of Infectious Diseases 1993* 168:1523–1527 (Dec. 1993).

Xing et al., "Second Generation Anti-MUC1 Peptide Monoclonal Antibodies," *Cancer Research* 52:2310–2317 (Apr. 15, 1992).

*Primary Examiner*—Marian C. Knode
*Assistant Examiner*—Donna C. Wortman
*Attorney, Agent, or Firm*—Jones & Askew

[57] ABSTRACT

The present invention provides antigenic peptides which bind anti-HCV antibodies for the differential diagnosis of acute and chronic HCV infection. The invention further provides a method of differentiating acute and chronic hepatitis C virus infection in a subject comprising: a) contacting an antibody-containing sample from the subject with one or more of the peptides selected from the group consisting of peptide 59, comprising the amino acids AFASRGNHVSPTHYVPESDA (SEQ ID NO:1), peptide 137, comprising the amino acids MNRLIAFASRGNHVSPTHYV (SEQ ID NO:2) and peptide 138, comprising the amino acids SRGNHVSPTHYVPESDAAAR (SEQ ID NO:3) under conditions that permit binding between the peptide and the antibodies; b) detecting the presence of binding between the peptide and the antibodies; c) contacting the antibody-containing sample from the subject with an amount of peptide 139, comprising the amino acids NHVSPTHYVPESDAAARVTA (SEQ ID NO:4) under conditions that permit binding between the peptide and the antibodies; d) detecting the presence of binding between the peptide and the antibodies; and comparing the strength of the antibody binding of step b) with the strength of the antibody binding of step d), a stronger binding in step b) as compared to the binding in step d) indicating acute hepatitis C virus infection and an equivalent binding in both steps b) and d) indicating chronic hepatitis C virus infection. The present invention further provides a method of diagnosing a hepatitis C virus infection in a subject comprising contacting an antibody containing sample from the subject with a peptide comprising the amino acids SPTHYV (SEQ ID NO:5) and determining the presence of binding between the peptide and the antibodies from the sample, the presence of binding between the peptide and the antibodies indicating a hepatitis C virus infection.

11 Claims, No Drawings

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Ala Phe Ala Ser Arg Gly Asn His Val Ser Pro Thr His Tyr Val Pro
1               5                   10                  15

Glu Ser Asp Ala
            20

( 2 ) INFORMATION FOR SEQ ID NO:2:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO (iv) ANTI-SENSE: NO (xi) SEQUENCE DESCRIPTION: SEQ ID NO:2:

Met Asn Arg Leu Ile Ala Phe Ala Ser Arg Gly Asn His Val Ser Pro
1               5                   10                  15

Thr His Tyr Val
            20

(2) INFORMATION FOR SEQ ID NO:3:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

Ser Arg Gly Asn His Val Ser Pro Thr His Tyr Val Pro Glu Ser Asp
1               5                   10                  15

Ala Ala Ala Arg
            20

(2) INFORMATION FOR SEQ ID NO:4:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

Asn His Val Ser Pro Thr His Tyr Val Pro Glu Ser Asp Ala Ala Ala
1               5                   10                  15

Arg Val Thr Ala
            20

(2) INFORMATION FOR SEQ ID NO:5:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:5:

Ser Pro Thr His Tyr Val
1               5

(2) INFORMATION FOR SEQ ID NO:6:

(i) SEQUENCE CHARACTERISTICS:
   (A) LENGTH: 10 amino acids
   (B) TYPE: amino acid
   (C) STRANDEDNESS: single
   (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:6:

```
Met Asn Arg Leu Ile Ala Phe Ala Ser Arg
1               5                   10
```

(2) INFORMATION FOR SEQ ID NO:7:

(i) SEQUENCE CHARACTERISTICS:
   (A) LENGTH: 10 amino acids
   (B) TYPE: amino acid
   (C) STRANDEDNESS: single
   (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:7:

```
Ile Ala Phe Ala Ser Arg Gly Asn His Val
1               5                   10
```

(2) INFORMATION FOR SEQ ID NO:8:

(i) SEQUENCE CHARACTERISTICS:
   (A) LENGTH: 10 amino acids
   (B) TYPE: amino acid
   (C) STRANDEDNESS: single
   (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:8:

```
Ala Phe Ala Ser Arg Gly Asn His Val Ser
1               5                   10
```

(2) INFORMATION FOR SEQ ID NO:9:

(i) SEQUENCE CHARACTERISTICS:
   (A) LENGTH: 12 amino acids
   (B) TYPE: amino acid
   (C) STRANDEDNESS: single
   (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:9:

```
Phe Ala Ser Arg Gly Asn His Val Ser Pro Gly Gly
1               5                   10
```

(2) INFORMATION FOR SEQ ID NO:10:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

```
Ala  Ser  Arg  Gly  Asn  Asn  Val  Ser  Pro  Thr  Gly
1                   5                        10
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

```
Ser  Arg  Gly  Asn  His  Val  Ser  Pro  Thr  His
1                   5                        10
```

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

```
Arg  Gly  Asn  His  Val  Ser  Pro  Thr  His  Tyr
1                   5                        10
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:13:

```
Gly  Asn  His  Val  Ser  Pro  Thr  His  Tyr  Val
1                   5                        10
```

( 2 ) INFORMATION FOR SEQ ID NO:14:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:14:

```
Asn His Val Ser Pro Thr His Tyr Val Pro Gly Gly
1               5                   10
```

(2) INFORMATION FOR SEQ ID NO:15:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:15:

```
His Val Ser Pro Thr His Tyr Val Pro Glu
1               5                   10
```

(2) INFORMATION FOR SEQ ID NO:16:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:16:

```
Val Ser Pro Thr His Tyr Val Pro Glu Ser
1               5                   10
```

(2) INFORMATION FOR SEQ ID NO:17:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:17:

```
Ser Pro Thr His Tyr Val Pro Glu Ser Asp
1               5                   10
```

(2) INFORMATION FOR SEQ ID NO:18:

(i) SEQUENCE CHARACTERISTICS:
 (A) LENGTH: 10 amino acids
 (B) TYPE: amino acid
 (C) STRANDEDNESS: single
 (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:18:

```
Pro Thr His Tyr Val Pro Glu Ser Asp Ala
1               5                   10
```

(2) INFORMATION FOR SEQ ID NO:19:

(i) SEQUENCE CHARACTERISTICS:
 (A) LENGTH: 10 amino acids
 (B) TYPE: amino acid
 (C) STRANDEDNESS: single
 (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:19:

```
Thr His Tyr Val Pro Arg Ser Asp Ala Ala
1               5                   10
```

(2) INFORMATION FOR SEQ ID NO:20:

(i) SEQUENCE CHARACTERISTICS:
 (A) LENGTH: 10 amino acids
 (B) TYPE: amino acid
 (C) STRANDEDNESS: single
 (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:20:

```
His Tyr Val Pro Glu Ser Asp Ala Ala Ala
1               5                   10
```

(2) INFORMATION FOR SEQ ID NO:21:

(i) SEQUENCE CHARACTERISTICS:
 (A) LENGTH: 10 amino acids
 (B) TYPE: amino acid
 (C) STRANDEDNESS: single
 (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:21:

```
Tyr Val Pro Glu Ser Asp Ala Ala Ala Arg
1               5                   10
```

(2) INFORMATION FOR SEQ ID NO:22:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:22:

```
Val  Pro  Glu  Ser  Asp  Ala  Ala  Ala  Arg  Val
1                   5                        10
```

( 2 ) INFORMATION FOR SEQ ID NO:23:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:23:

```
Pro  Glu  Ser  Asp  Ala  Ala  Ala  Arg  Val  Thr
1                   5                        10
```

( 2 ) INFORMATION FOR SEQ ID NO:24:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:24:

```
Ser  Asp  Ala  Ala  Ala  Arg  Val  Thr  Leu  Ser
1                   5                        10
```

( 2 ) INFORMATION FOR SEQ ID NO:25:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:25:

```
Gly  Gly  Ser  Arg  Gly  Asn  His  Val  Gly  Gly
1                   5                        10
```

( 2 ) INFORMATION FOR SEQ ID NO:26:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:26:

```
Gly  Gly  Arg  Gly  Asn  His  Val  Ser  Gly  Gly
 1                  5                        10
```

( 2 ) INFORMATION FOR SEQ ID NO:27:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:27:

```
Gly  Gly  Gly  Asn  His  Val  Ser  Pro  Gly  Gly
 1                  5                        10
```

( 2 ) INFORMATION FOR SEQ ID NO:28:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:28:

```
Gly  Gly  Asn  His  Val  Ser  Pro  Thr  Gly  Gly
 1                  5                        10
```

( 2 ) INFORMATION FOR SEQ ID NO:29:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:29:

```
Gly  Gly  His  Val  Ser  Pro  Thr  His  Gly  Gly
 1                  5                        10
```

( 2 ) INFORMATION FOR SEQ ID NO:30:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:30:

```
Gly Gly Val Ser Pro Thr His Tyr Gly Gly
 1               5                   10
```

( 2 ) INFORMATION FOR SEQ ID NO:31:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:31:

```
Gly Gly Ser Pro Thr His Tyr Val Gly Gly
 1               5                   10
```

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:32:

```
Gly Gly Pro Thr His Tyr Val Pro Gly Gly
 1               5                   10
```

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:33:

```
Gly Gly Thr His Tyr Val Pro Glu Gly Gly
 1               5                   10
```

( 2 ) INFORMATION FOR SEQ ID NO:34:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:34:

```
Gly  Gly  His  Tyr  Val  Pro  Glu  Ser  Gly  Gly
 1              5                        10
```

( 2 ) INFORMATION FOR SEQ ID NO:35:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:35:

```
Gly  Gly  Tyr  Val  Pro  Glu  Ser  Asp  Gly  Gly
 1              5                        10
```

( 2 ) INFORMATION FOR SEQ ID NO:36:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:36:

```
Gly  Gly  Val  Pro  Glu  Ser  Asp  Ala  Gly  Gly
 1              5                        10
```

( 2 ) INFORMATION FOR SEQ ID NO:37:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:37:

```
Gly  Gly  Pro  Glu  Ser  Asp  Ala  Ala  Gly  Gly
 1              5                        10
```

( 2 ) INFORMATION FOR SEQ ID NO:38:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:38:

Ser Arg Gly Asn His Val Ser Pro Thr His Tyr Val Pro Glu Ser Asp
 1               5                   10                  15
Ala ( 2 ) INFORMATION FOR SEQ ID NO:39:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:39:

His Val Ser Pro Thr His Tyr Val Pro Glu Ser
 1               5                   10

( 2 ) INFORMATION FOR SEQ ID NO:40:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:40:

His Tyr Val Pro Glu Ser
 1               5

METHODS AND COMPOSITIONS FOR DIFFERENTIAL DIAGNOSIS OF ACUTE AND CHRONIC HEPATITIS C VIRUS INFECTION

BACKGROUND OF THE INVENTION

1. Field of the Invention

The invention pertains to compositions and methods for differential diagnosis of early (acute) and late (chronic) hepatitis C virus (HCV) infection in a subject. The compositions include antigenic peptides of HCV. The methods include serological diagnosis of HCV infection and differentiation of HCV infection as either acute or chronic.

2. Background Art

The hepatitis C virus (HCV) is a major causative agent of parenterally transmitted non-A, non-B hepatitis worldwide (1,7). The HCV genome consists of a 9.4 kb positive sense RNA molecule that contains one large open reading frame capable of encoding a polyprotein of 3010 or 3011 amino acids (2). The HCV structural proteins, especially the nucleocapsid protein, have been found to contain broadly reactive antigenic epitopes (4,6,9,17,18) and have been incorporated into most of the available diagnostic test systems (5,9,10,11,19,20,23).

The nonstructural proteins NS3 and NS4 also contain strongly reactive antigenic epitopes and recombinant polypeptides derived from these proteins have been employed in diagnostic tests (5,8). Synthetic peptides have been used to characterize the antigenic composition of the nonstructural proteins, including NS4, which has been determined to contain a major antigenic region, 5-1-5, which contains at least two antigenic epitopes (3,12).

Currently available assays for diagnosing HCV infection demonstrate only that a subject has been exposed to the virus at some point in his life. An assay for differential diagnosis of HCV infection as either acute or chronic infection would provide a clinician with information such as whether an infection is primary or secondary. A primary infection occurs during the acute infection phase and may or may not be manifested clinically. A secondary infection can occur years later in a subject who has been a chronic HCV carrier. The differentiation between acute (primary) and chronic (secondary, tertiary, etc.) infection can guide the clinician in determining when various therapy regimens can be initiated. In addition, a differential assay will distinguish primary infections for clinical trials of various therapeutics. A phase-discriminatory test for HCV infections is particularly important because of the apparent difficulties associated with the use of IgM anti-HCV activity as a marker of recent infection (13).

The present invention provides such a phase-discriminating test by providing antigens from a newly identified C-terminal region, which contains a very strong and broadly reactive B-cell epitope(s). The antigenic properties of this region have been examined by analysis of a panel of 150 synthetic peptides spanning more than 90% of the NS3–NS4–NS5 region of the HCV polyprotein. From this study, a complex pattern of IgG immune response within this region was identified, demonstrating that certain epitopes elicit antibodies at different durations during the course of HCV infection. In particular, three peptides were identified which strongly reacted with antibody at the early stage of HCV infection, while a fourth peptide demonstrated a noticeably delayed reactivity. Thus, this invention provides specific peptide sequences from the C-terminal region of the HCV NS4 protein which are used in an immunoassay to differentiate early (acute) and late (chronic) HCV infection.

SUMMARY OF THE INVENTION

The present invention provides antigenic peptides which bind anti-HCV antibodies for the differential diagnosis of acute and chronic HCV infection.

The invention further provides a method of differentiating acute and chronic hepatitis C virus infection in a subject comprising: a) contacting an antibody-containing sample from the subject with one or more of the peptides selected from the group consisting of peptide 59, comprising the amino acids AFASRGNHVSPTHYVPESDA (SEQ ID NO:1), peptide 137, comprising the amino acids MNRLIAFASRGNHVSPTHYV (SEQ ID NO:2) and peptide 138, comprising the amino acids SRGNHVSPTHYVPESDAAAR (SEQ ID NO:3) under conditions that permit binding between the peptide and the antibodies; b) detecting the presence of binding between the peptide and the antibodies; c) contacting the antibody-containing sample from the subject with an amount of peptide 139, comprising the amino acids NHVSPTHYVPESDAAARVTA (SEQ ID NO:4) under conditions that permit binding between the peptide and the antibodies; d) detecting the presence of binding between the peptide and the antibodies; and comparing the strength of the antibody binding of step b) with the strength of the antibody binding of step d), a stronger binding in step b) as compared to the binding in step d) indicating acute hepatitis C virus infection and an equivalent binding in both steps b) and d) indicating chronic hepatitis C virus infection.

The present invention further provides a method of diagnosing a hepatitis C virus infection in a subject comprising contacting an antibody-containing sample from the subject with a peptide comprising the amino acids SPTHYV (SEQ ID NO:5) and determining the presence of binding between the peptide and the antibodies from the sample, the presence of binding between the peptide and the antibodies indicating a hepatitis C virus infection.

DETAILED DESCRIPTION OF THE INVENTION

The present invention may be more readily understood by reference to the following detailed description of specific embodiments and the Examples included herein.

SERODIAGNOSTIC METHODS

In one embodiment, the present invention provides a method of differentiating acute and chronic HCV infection in a subject comprising contacting an antibody-containing sample from the subject with an amount of one or more of the peptides selected from the group consisting of peptide 59, comprising the amino acids AFASRGNHVSPTHYVPESDA (SEQ ID NO:1 ), peptide 137, comprising the amino acids MNRLIAFASRGNHVSPTHYV (SEQ ID NO:2) and peptide 138, comprising the amino acids SRGNHVSPTHYVPESDAAAR (SEQ ID NO:3) under conditions that permit binding between the peptide and the antibodies; detecting the presence of binding between the peptides and an antibody in the subject's sample; contacting an antibody-containing sample from the subject with an amount of peptide 139, comprising the amino acids NHVSPTHYVPESDAAARVTA (SEQ ID NO:4) under conditions that permit binding between the peptide and the antibodies; detecting the presence of binding between the peptide and the antibodies; and comparing the strengths of the antibody binding in the two steps to determine if acute or chronic HCV infection is present in the subject. In the method in which more than one of the peptides 59, 137 and 138 are contacted with the antibody-containing sample, the peptides can be contacted separately. Alternatively, they may be contacted together with the same sample. The peptides used in this method can be any of the peptides 59, 137, 138 and 139 or modified versions thereof that maintain reactivity with antibodies against HCV as further described below.

As used herein, "binding between the peptide and the antibodies" means the formation of a complex between the peptide and the antibody or antibodies which specifically react with that peptide. A binding reaction that exhibits strength above an empirically determined background (random binding) level is considered specific. As used herein, "strength of the antibody binding" means a quantitative measurement of any binding reaction between the peptides and antibodies present in the subject's sample. For example, in an EIA assay (see Examples), the optical density value of a sample after completion of all the reaction steps in a reaction well is a quantitative measurement of the binding reaction between the antigen and antibody in the well. Other quantitative measurements of the strength of binding between the peptide and antibodies can include quantitative immunofluorescence assays, immunoblotting assays and agglutination/precipitation assays, among others. Also, as used herein, "stronger binding" means a ratio value greater than 2.0 or an empirically determined cutoff value wherein the ratio is a quantitative comparison of immunoreactivity between peptides which react strongly with antibody at the acute stage of HCV infection (e.g. peptides 59, 137 and 138) and peptides which show a delayed reactivity (e.g. peptide 139). For example, chronic HCV infection samples analyzed in the present invention showed ratios of optical density values between peptides 59 and 139 ranging from 0.33 to 1.87, while acute HCV infection samples demonstrated ratios between peptides 59 and 139 ranging from 2.52 to 35.40 (see Examples). As used herein, "equivalent binding" means a ratio value around 1.0 and generally less than 2.0, wherein the ratio is a quantitative comparison of immunoreactivity between peptides which react strongly with antibody at the acute stage of HCV infection (e.g. peptides 59, 137 and 138) and peptides which show a delayed reactivity (e.g. peptide 139). The optical density value ratios provided herein that demonstrate acute or chronic HCV infection can be standardized for comparison to other quantitative methods such as quantitative immunofluorescence assays, immunoblotting assays and agglutination/precipitation assays, among others. As used herein, "acute hepatitis C virus infection" means the primary stage of an HCV infection during which the immune system elicits an initial response to recent introduction of HCV into a subject and "chronic hepatitis C virus infection" means any stage of an HCV infection beyond the primary episode.

In a further embodiment, the present invention provides a method of diagnosing the presence or absence of a hepatitis C virus infection in a subject comprising contacting an antibody containing sample from the subject with a peptide comprising the amino acids SPTHYV (SEQ ID NO:5) and determining the presence of binding between the peptide and the antibodies from the sample, the presence of binding between the peptide and the antibodies indicating a hepatitis C virus infection and the absence of binding indicating the lack of a hepatitis C virus infection. The peptides used in this method can be any of the peptides 59, 137, 138 and 139 or modified versions thereof that maintain reactivity with antibodies against HCV as further described below.

IMMUNOASSAYS

Immunoassays such as immunofluorescence assays (IFA), enzyme linked immunosorbent assays (ELISA) and immunoblotting can be readily adapted to accomplish the detection of the HCV antibodies. An ELISA method effective for the detection of the antibodies can, for example, be as follows: (1) bind the antigen to a substrate; (2) contact the bound antigen with a fluid or tissue sample containing the antibody; (3) contact the above with a secondary antibody bound to a detectable moiety which is reactive with the bound antibody (e.g., horseradish peroxidase enzyme or alkaline phosphatase enzyme); (4) contact the above with the substrate for the enzyme; (5) contact the above with a color reagent; (6) observe color change.

COMPETITIVE INHIBITION ASSAY

Another immunologic technique that can be useful in the differentiation of acute and chronic HCV infection utilizes monoclonal antibodies (MAbs) for detection of antibodies specifically reactive with HCV antigen. Briefly, serum from the subject is reacted with the antigen bound to a substrate (e.g., an ELISA 96-well plate). Excess serum is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

MICRO-AGGLUTINATION ASSAY

A micro-agglutination test can also be used to differentiate acute and chronic HCV infection in a subject. Briefly, latex beads, red blood cells or other agglutinable particles are coated with the peptide which has been conjugated to a moiety that renders the peptide polyvalent, and mixed with a sample from the subject, such that antibodies in the tissue or body fluids that are specifically reactive with the peptide crosslink with the peptide, causing agglutination. The agglutinated peptide-antibody complexes form a precipitate, visible with the naked eye or by spectrophotometer.

SANDWICH ASSAY/FLOW CYTOMETRY/ IMMUNOPRECIPITATION

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides HCV antigen for the differentiation of acute and chronic HCV infection, other serological methods such as flow cytometry and immunoprecipitation can also be used as detection methods.

In the diagnostic methods taught herein, the antigen can be bound to a substrate and contacted by a fluid sample such as blood, serum, urine or saliva. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.

DETECTABLE MOIETIES

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy), alkaline phosphatase (for biochemical detection by color change) and radioactive isotopes (for autoradiography, fluorography and radiometric detection).

ANTIGENS

The present invention provides antigenic peptides of HCV. The peptides generally exist in a purified form. As used herein, "purified" means the peptide is sufficiently separated from other viral or cellular contaminants to be useful in a clinical or research setting (e.g. in a diagnostic assay). Various levels of purification can be achieved using known methods. The purified antigenic HCV peptides of the present invention are also referred to herein as "the antigen" or "the HCV antigen" and are designated interchangeably by either peptide number or SEQ ID NO.

The peptides of the present invention can comprise the amino acids contained in the amino acid sequences defined in the Sequence Listing by SEQ ID NOS:1,2,3,4 or 5. Thus, the peptides of the invention can have the same sequence as found in the Sequence Listing. The peptides of the present invention can be unconjugated, or they can be conjugated, for example, to a moiety which imparts polyvalence to the peptide for use in agglutination assays or to a carrier protein that facilitates placement of the peptide on the solid phase. A carrier protein is one to which synthetic peptides can be conjugated and which will not react with antibodies in human serum. An example of such a carrier is bovine serum albumin (BSA).

By providing the amino acid sequence of the present immunoreactive peptides, it is possible to synthesize, using the methods taught herein and standard peptide synthesis techniques, other peptides chosen to be homologous to immunoreactive regions of the specifically recited peptides and to modify these peptides by inclusion, deletion or modification of particular amino acid residues in the derived sequences. For Example, the core sequence SPTHYV (SEQ ID NO:5) has been determined to be immunoreactive. Based on this core sequence, peptides of various lengths can be derived from the native sequence of this region of the HCV genome, and synthesized, which contain nonessential amino acid substitutions which do not substantially reduce or alter the specificity or immunoreactivity of the core sequence for HCV. For example, conservative amino acid substitutions can be incorporated which preserve the acidic or basic characteristics of the peptide. Peptides synthesized in this manner can be determined to be similarly immunoreactive to the core sequence by the methods taught herein, such as an ELISA (see Examples). Thus, synthesis or purification of an extremely large number of peptides derived from the disclosed C-terminus of the NS4 protein is possible.

The amino acid sequences of the present peptides can contain an immunoreactive portion of HCV antigen (e.g. SEQ ID NO:1–5) attached to sequences designed to provide for some additional property, such as solubility as taught herein. The amino acid sequences of the HCV antigens can include sequences in which one or more amino acids have been substituted with another amino acid to provide for some additional property, such as to remove/add amino acids capable of disulfide bonding to increase the reactivity of an epitope by providing a more rigid secondary structure, to increase its bio-longevity, to alter its cytotoxicity or to prevent infection. In any case, the peptide must possess immunoreactivity and immunogenicity.

The purified peptides thus obtained can be tested to determine their antigenicity and specificity (for HCV antibodies or for acute or chronic phase HCV antibodies) by the methods taught herein, such as ELISA (see Examples). An immunoreactive peptide is defined as an amino acid sequence, which binds an anti-HCV antibody, of at least six consecutive amino acids and up to any number of consecutive amino acids derived from the C-terminus region of the native NS4 protein. For example, the peptides can range from 6–100 amino acids in length (e.g. 20 amino acids). The peptides of the present invention can also be recombinant proteins obtained by cloning nucleic acids encoding the peptide in an expression system capable of producing the antigenic peptide. Alternatively, an antigenic peptide can be isolated from the whole protein by chemical or mechanical disruption.

PEPTIDE COMBINATIONS

The present invention also provides the combination of two or three of the peptides defined in the Sequence Listing as SEQ ID NO:1, SEQ ID NO:2 and SEQ ID NO:3 in the method of differentiating acute and chronic hepatitis C virus infection in a subject. In addition to the individual peptides, the combinations of peptides of the present invention can also be referred to herein as "the antigen" or "the HCV antigen." As with the individual peptides, the combinations of peptides of this invention can comprise conjugated peptides, unconjugated peptides or both. Furthermore, the conjugated peptides of the invention can be amounts of an individual peptide conjugated to a carrier or amounts of different peptides conjugated to a single carrier. The combinations, as well as the individual peptides, can be attached or bound to a substrate (solid phase) and can be used in diagnosing HCV infection.

DETERMINING ANTIGENICITY/ IMMUNOREACTIVITY

A method of selecting alternative peptides having specific immunoreactivity with an antibody reactive with the peptides of this invention is also provided. For example, such a method for determining the minimal sequence for immunoreactivity of a peptide having immunoreactivity with an antibody reactive with HCV includes the following steps: (a) modifying a peptide of the present invention; (b) contacting the modified peptide with a confirmed HCV positive serum sample from a subject; and (c) detecting the binding of the modified peptide and anti-HCV antibody, the binding indicating that the modified peptide has immunoreactivity with HCV. An example of this method, which can be applied to the other peptides of the present invention, is illustrated in the Examples. Any of the peptides of the invention can likewise be modified.

RECOMBINANT MOSAIC PROTEINS

Because the present invention provides the amino acid sequences of antigenic peptides and their nucleic acid coding sequences in the HCV genome (2), a recombinant mosaic protein can be produced comprising a plurality of the peptides of the present invention. The protein can include any one or more of the epitopes of peptides 59, 137, 138 and 139 among others, and can also include additional amino acids that do not substantially affect the antigenicity or specificity of the protein. This mosaic protein is highly sensitive and specific because of the absence of extraneous amino acids that can interfere with the presentation of the epitopes. It is contemplated that the mosaic proteins of this invention can be used, as described herein, for diagnostic tests and vaccines. The currently preferred method of expressing the mosaic protein is by means of vector-host expression systems.

PURIFIED ANTIBODIES

A purified monoclonal antibody specifically reactive with the antigen is also within the scope of the invention. The antibodies can be specifically reactive with a unique epitope of the antigen or they can also react with epitopes of other organism. The term "reactive" means capable of binding or otherwise associating nonrandomly with an antigen. "Specifically reactive" as used herein describes an antibody or other ligand that does not cross react substantially with any antigen other than the one specified, in this case, the HCV antigen. Antibodies can be made as described in Harlow and Lane (14). Briefly, purified antigen can be injected into an animal in an mount and in intervals sufficient to elicit an immune response. Antibodies can either be purified directly, or spleen cells can be obtained from the animal. The cells are then fused with an immortal cell line and screened for antibody secretion. The antibodies can be used to screen DNA done libraries for cells secreting the antigen. Those positive clones can then be sequenced (15,16). Purified nonhuman, preferably mammalian, polyclonal antibodies reactive with the HCV antigenic peptides provided herein are also contemplated. The polyclonal antibody can also be obtained by the standard immunization and purification protocols (14).

The antibody can be bound to a substrate or labeled with a detectable moiety or both bound and labeled. The detectable moieties contemplated with the composition of the present invention are those listed in the description of the diagnostic methods, including fluorescent, enzymatic and radioactive markers.

VACCINES

The purified peptide fragments thus obtained can be conjugated to structural peptides which elicit neutralizing antibodies and tested to determine their immunogenicity and specificity for use in a vaccine. Briefly, various concentrations of a putative immunogenically specific peptide are prepared and administered to an animal and the immunological response (i.e., the production of antibodies) of an animal to each concentration is determined. The mounts of immunogen administered depend on the subject, e.g., a human or other susceptible animal, the condition of the subject, the size of the subject, etc. Thereafter an infection-susceptible animal so inoculated with the immunogen can be exposed to the virus to test the potential vaccine effect of the specific immunogenic peptide. The specificity of a putative immunogenic peptide can be ascertained by testing sera or other fluid from the inoculated animal for cross reactivity with other closely related viruses. Alternatively, the immunogenicity can be tested in an in vitro method using serum from the immunized animal to attempt to neutralize infectious virus, which can then be added to cell culture to determine if the peptide elicited neutralizing antibodies.

The antigen of this invention can be used in the construction of a vaccine comprising an immunogenic mount of the antigen and a pharmaceutically acceptable carrier. The pharmaceutically acceptable carrier in the vaccine of the instant invention can comprise saline or other suitable carriers (22). An adjuvant can also be a part of the carrier of the vaccine, in which case it can be selected by standard criteria based on the antigen used, the mode of administration and the subject (22). Methods of administration can be by oral or sublingual means, or by injection, depending on the particular vaccine used and the subject to whom it is administered.

It can be appreciated from the above that the vaccine can be used as a prophylactic or a therapeutic. Thus, the invention provides methods of preventing or treating an HCV infection and the associated disease by administering the vaccine to a subject.

The following examples are intended to illustrate, but not limit, the invention. While they are typical of those that might be used, other procedures known to those skilled in the art may be alternatively employed.

EXAMPLES

Synthetic peptides.

Peptides were synthesized by FMOC chemistry (21) on an ACT Model MPS 350 multiple peptide synthesizer (Advanced Chemtech, Louisville, Ky. according to the manufacturer's protocols. After characterization by amino acid analysis, high performance liquid chromatography, and capillary electrophoresis, peptides were characterized by enzyme immunoassay.

Sera.

All anti-HCV-positive sera were obtained from a collection reposited at the D.I. Ivanovsky Institute of Virology, Moscow, Russia. Serum specimens were collected from 25 anti-HCV-positive patients with acute liver disease (n=36) and from 28 anti-HCV-positive patients with chronic liver disease (n=43). Anti-HCV-negative serum specimens (n=32) from normal blood donors were obtained from a collection reposited at the Centers for Disease Control and Prevention. All sera were initially tested by commercially available kits (ABBOTT Laboratories, Abbott Park, Ill.) for markers of hepatitis B and hepatitis D infection, and for the presence of anti-HCV activity.

Enzyme immunoassay (EIA) for anti-HCV.

Synthetic peptides (110 µl) at a concentration of 10 µg/ml in 0.1M phosphate-buffered saline (PBS), pH 7.5, were adsorbed to microtiter wells (Immulon II, Dynatech Laboratories, Inc.) at room temperature for 12 h. Sera were diluted 1:50 in PBS containing 0.1% Tween 20 and 10% normal goat serum (PBS-T). One hundred µl of diluted sera was added to each well and incubated for 1 hr at 37 C. Binding of antibodies to the peptides was identified with affinity purified antibodies to human IgG coupled to horseradish peroxidase (Boehringer Mannheim, Indianapolis, Ind.) by adding 100 µl of a 1:30,000 dilution in PBS-T and incubating for 1 hr at 37 C. Several cutoffs were established for acute and chronic anti-HCV-positive sera. In experiments that used 20-mer synthetic peptides, the cutoff, expressed as a P/N ratio and equal to 3.0, was statistically established as the mean of negative controls plus 5.5 standard deviations (SD) above the mean, where P represents the optical density value at 493 nm ($OD_{493}$) of anti-HCV-positive specimens and N represents the optical density value of negative controls. In experiments that used 6-mer or 10-mer peptides, a higher cutoff was used to ensure statistical reliability and accurate interpretation of positive results. In this case, the cutoff, expressed as a P/N ratio and equal to 5.0, corresponded to the mean of negative controls plus 14 SD above the mean. For peptide SEQ ID NO:17, a cutoff equal to a P/N value of 5.0 was used; however, this peptide demonstrated a wider range of reactivity with negative sera and the cutoff was equal to only 5.5 SD above the mean.

HCV seroconversion panels.

All four HCV seroconversion panels were obtained from Serologicals, Inc. (Clarkston, Ga.). All samples from these panels were obtained as undiluted sera and not heat inactivated. Panel 4811 contained 21 serial plasma samples collected over a period of 378 days. Donor 4811 is a 46-year-old female who received a blood transfusion 14 days prior and again 11 days after the first date of collection. An elevation of alanine aminotransferase (ALT) was first observed 28 days after the first transfusion. The ALT values fluctuated throughout the duration of the plasma collections, but returned to normal levels by the end of the plasma donation period. The donor showed no clinical signs of disease throughout the donation period. Donor 4811 tested negative for anti-human immunodeficiency virus (anti-HIV), anti-hepatitis B core antigen (anti-HBc), and anti-hepatitis B surface antigen (anti-HBs) antibodies. This donor was positive for IgG specific to hepatitis A virus (HAV), cytomegalovirus (CMV), and Epstein-Barr virus (EBV).

Panel 4812 contained 22 serial plasma samples collected over a period of 333 days. Donor 4812 is a 33-year-old female who received an intravenous blood transfusion 10, 9, and 7 days prior to the first collection date. Within 35 days of the first transfusion, donor 4812 demonstrated an elevation in ALT, which fluctuated throughout the duration of the plasma collections, but returned to normal by the end of the plasma donation period. The donor showed no clinical signs of disease throughout the donation period and tested negative for anti-HIV, anti-HAV, anti-HBc, and anti-HBs antibodies. Donor 4812 tested positive for IgG to CMV and EBV.

Panel 4813 contained 22 serial plasma samples collected over a period of 400 days. Donor 4813 is a 67 year old female who received whole blood on the day when the first sample was collected. Within 39 days, donor 4813 developed an elevation in ALT, which fluctuated throughout the duration of the plasma collections, but returned to normal by the end of the plasma donation period. The donor showed no clinical signs of disease throughout the donation period and tested negative for anti-HIV, and anti-HBc antibodies. This donor tested positive for IgG to CMV and EBV.

Panel 4814 contains 13 serial plasma samples collected over a period of 137 days. Donor 4814 is a 28-year-old male who received a blood transfusion 57, 50, and 35 days before the first collection date. Within 90 days of the first transfusion, donor 4814 developed an ALT elevation, which fluctuated throughout the duration of the plasma collections, but returned to normal by the end of the plasma donation period. The donor showed no clinical signs of disease throughout the donation period and tested negative for anti-HIV, anti-HBc, and anti-HBs antibodies.

Temporal pattern of HCV-specific IgG reactivity with synthetic peptides derived from the C-terminus of the HCV NS4 protein.

Synthetic peptides 59, 137, 138, and 139, that cover the region from amino acid positions 1916 to 1946 of the HCV polyprotein (Table 1), were tested with the four above-described HCV seroconversion panels obtained from four individuals infected with HCV following blood transfusion. Each peptide was individually tested with each member of the seroconversion panels. In each panel, all four peptides were reactive with HCV-specific IgG antibody. However, the patterns of immunoreactivity for these peptides differed. Peptides 59 and 137 reacted with antibodies during the early stages of HCV infection, when the ALT values were elevated. These peptides also demonstrated the strongest immunoreactivity as indicated by the OD values. Peptide 139 was less immunoreactive. The reaction of the peptide was noticeably weaker than that of any of the other peptides, especially with antibodies from serum specimens obtained before the first 100 to 150 days following blood transfusion. Peptide 138 demonstrated intermediate strength of reactivity with each seroconversion panel. Thus, peptides 59 and 137 reacted relatively strongly with anti-HCV IgG during the early stage of infection, whereas peptide 139 reacted relatively weakly during the early stage of infection and increased in strength during the later stage of infection. This pattern was observed with each HCV seroconversion panel except panel 4814, which did not contain a sufficient number of follow-up serum specimens. Nonetheless, this panel confirmed the observation that during the first 120 days after transfusion, peptide 139 exhibited a lower reactivity compared to peptides of the first group.

Relative antigenic reactivity of peptides 59 and 139 with sera obtained from acutely or chronically HCV-infected persons.

The data obtained with all four seroconversion panels indicated that during the first 100 to 150 days of HCV infection the ratio of immunoreactivity of peptides 59, 137, or 138 to the immunoreactivity of peptide 139 was higher during the early stages of infection than ratios obtained later in the infection. This ratio can be used to discriminate acute from chronic HCV infection.

To further validate the observation that a ratio of peptide immunoreactivity may vary in a stage-specific manner during HCV infections, two additional panels of sera were analyzed. One panel was composed of 36 serum specimens obtained from 25 anti-HCV-positive patients with acute hepatitis. The other panel contained 43 serum specimens from 31 anti-HCV-positive patients with chronic liver disease. Each sample was tested with synthetic peptides 59, 137, 138, and 139. $OD_{493}$ values were used as a measure of peptide immunoreactivity. The reactivity of peptides 59, 137, and 138 with sera from patients with acute hepatitis was usually higher than that of peptide 139, while the reactivity of peptides 59, 137, and 138 with sera from patients with chronic HCV infections was usually equal to or lower than the reactivity of peptide 139. The best discrimination between acute and chronic samples could be achieved by developing a ratio of immunoreactivity between peptides 59 and 139. Among the 36 specimens from patients with acute liver disease, only four (three serum specimens from one patient and one specimen from another) had 59/139 ratios very close to 1.0 or significantly less than 1.0. For the other 32 specimens from 23 acutely infected patients the mean of the 59/139 ratio was 7.91 (range: 2.52–35.40). Among the 43 specimens obtained from 31 chronically infected patients, 40 specimens from 28 patients yielded a mean ratio equal to 1.01 (range: 0.33–1.87). Three specimens from three different patients had 59/139 ratio of 2.99, 4.59 and 6.64, respectively. Based on a cutoff of 1.01 plus 3.5 SD, 23 of 25 patients with acute hepatitis and 3 of 31 patients with chronic hepatitis may be diagnosed with acute or recent HCV infection. Thus, this cutoff allowed for the identification of 92.0% of acute and 90.3% of chronic HCV infections used in this study. The discrepancies found within each group may be due to genetic variation in the ability of individuals to respond to the antigenic epitope(s) represented within peptides 59 and 139. For example, sera obtained from the two acutely infected patients who demonstrated low 59/139 ratios did not react strongly with any of the peptides used in this study. On the other hand, ratios exceeding the cutoff for the three chronically infected patients might be associated with exacerbations of HCV infection.

Antigenic epitope(s) within the C-terminal region of the NS4 protein.

Data obtained with synthetic peptides 59, 137, 138, and 139 suggested that this region of the NS4 protein has a more complex antigenic structure than anticipated. The difference in the temporal profiles of antibodies reactive with these peptides suggested that this region may contain more than one antigenic epitope. To characterize the antigenic composition of this region in greater detail, two additional sets of overlapping synthetic peptides were synthesized (Tables 2 and 3). One set was composed of 10-mer synthetic peptides, while the second set contained only 6-mer HCV-specific sequences flanked by two glycines at the N- and C-terminus of each peptide. For analysis of immunoreactivity, serum specimens were selected from the panels of anti-HCV-positive patients with acute (n=5) and chronic (n=17) hepatitis that were used for the characterization of the relative reactivity of peptides 59 and 139 (see above). Sera were selected on the basis of their strong immunoreactivity. In addition, 32 anti-HCV-negative sera were also tested with each peptide from these two additional sets (Tables 2 and 3).

The set of immunoreactive 10-mer synthetic peptides covered a 17 amino acid region of the HCV NS4 protein comprising the sequence SRGNHVSPTHYVPESDA (SEQ ID NO:38), and the set of immunoreactive peptides containing six amino acid HCV-specific sequences covered an 11 amino acid region comprising the sequence HVSPTHYVPES (SEQ ID NO:39) (Tables 2 and 3). Both regions contain the sequence SPTHYV (SEQ ID NO:5), which has been recently identified as an important component of the antigenic epitope(s) located within the C-terminus of the HCV NS4 protein. Since the immunoreactive peptides SEQ ID NO:29 and SEQ ID NO:34 are overlapped by only one amino acid and, therefore, can not share an epitope (Table 3), it may be concluded that this region contains more than one antigenic epitope. Furthermore, a comparison of the pattern of reactivity of serum specimens with both sets of short synthetic peptides suggested that more than two antigenic epitopes may exist within this region. For example, serum specimen 6 reacted with several 10-mer peptides but with none of the 6-mer peptides, whereas specimen 8 did not react with any 10-mer peptide, but did react with the 6-mer peptide SEQ ID NO:32. This observation suggested that one epitope may be mimicked with peptides of one size, and the other epitope may be mimicked with peptides of another size. All sera included in Tables 2 and 3 were immunoreactive with peptide 59; however, short synthetic peptides failed to react with some of these sera, indicating the presence of an antigenic epitope (s) within this region that may be functionally imitated only with a longer peptide. Peptide SEQ ID NO:34 is another interesting example of a B-cell epitope that can be functionally modeled with peptides of only one size (Table 3). This peptide contains the HCV-specific sequence HYVPES (SEQ ID NO:40). This sequence is completely represented within several 10-mer peptides (Table 2). However, two of these 10-mers did not react with any anti-HCV-positive sera used in this study. Collectively, these data suggested that several antigenic epitopes are located within this region and some of them can be modeled in an antigenically active form with peptides of only one size.

An analysis of subsets of sera demonstrating specific immunoreactivity with different synthetic peptides provided additional evidence on the complex antigenic composition of the NS4 region. All immunoreactive 10-mer and 6-mer peptides reacted with different subsets of sera. Because of significant sharing of amino acid sequences in some overlapping peptides, these peptides may share the same antigenic epitope(s), and, therefore, should result in very similar or identical patterns of reactivity. For example, peptides 59 and 137 demonstrated strong immunoreactivity with all sera in Tables 2 and 3. This finding implies that these peptides have very similar B-cell epitope compositions. However, short synthetic peptides demonstrated a pattern of reactivity with these sera that was unique for each individual peptide (Tables 2 and 3). For example, peptide SEQ ID NO:32 reacted with 15 out of 32 sera. This peptide shares at least four amino acids with peptides SEQ ID NO:30, SEQ ID NO:31, SEQ ID NO:33, and SEQ ID NO:34. Nonetheless, these peptides failed to demonstrate an identical or very close pattern of reactivity with anti-HCV-positive sera (Table 3). Similar results were obtained with other peptides presented in Tables 2 and 3.

Variation in the temporal pattern of the HCV-specific IgG reactivity with short synthetic peptides.

Both sets of short synthetic peptides were tested with the four seroconversion panels. Most immunoreactive peptides identified previously (Tables 2 and 3) also demonstrated some immunoreactivity with serum specimens from these seroconversion panels. Each seroconversion panel immunoreacted, however, with a different subset of peptides, a finding that supports the observation made above. For example, panel 4811 demonstrated reactivity with 10-mer peptides SEQ ID NOS:12–17, panel 4812 with peptides SEQ ID NO:11–13, panel 4813 with peptides SEQ ID NO:11–17, and panel 4814 with peptides SEQ ID NO:13–16. Similar results were obtained with 6-mer peptides.

Analysis of the temporal pattern of peptide reactivity with antibodies identified three additional characteristics of the IgG immune response to this region of the NS4 protein.

First, this small region of less than 20 amino acids contains antigenic epitopes that elicit IgG antibodies at different times. All four panels demonstrated two patterns of IgG reactivity with these short synthetic peptides: early and late. For example, peptides SEQ ID NO:31 and SEQ ID NO:32 reacted with sera from panel 4811 at different times. Similar patterns were observed for peptides SEQ ID NO:29 and SEQ ID NO:32 with sera from panel 4812, peptides SEQ ID NO:12 and SEQ ID NO:14 with sera from panel 4813, and peptides SEQ ID NO:13 and SEQ ID NO:30 with sera from panel 4814. In addition, IgG profiles obtained with short peptides were different from the patterns obtained with the longer peptides 59, 137, and 138. These longer peptides always reacted with antibodies during the first ALT elevation, whereas the short synthetic peptides, at least with panels 4813 and 4814, reacted at a later stage of HCV infection. This observation is also applicable, to some extent, to seroconversion panel 4811, and implies that 20-mer peptides may imitate early antigenic epitope(s) that are not modeled with shorter ones. Second, antibodies reacting with 10-mer and 6-mer synthetic peptides tend to be detectable for a relatively short period of time, whereas antibodies reactive with 20-mer peptides remain reactive over the entire period of observation. Third, 6-mer peptides that overlap by five amino acids (e.g., peptides SEQ ID NO:31 and SEQ ID NO:32) may have very different patterns of temporal immunoreactivity.

Through the above type of analysis, it is routine to test the above peptides with non-essential amino acid substitutions to determine their immunoreactivity levels and ability to differentiate acute and chronic HCV infection.

TABLE 1

AMINO ACID SEQUENCE AND LOCATION OF 20-MER PEPTIDES DERIVED FROM THE C-TERMINAL REGION OF THE HCV NS4 PROTEIN

| SEQ ID NO: | PEPTIDE | LOCATION, aa | SEQUENCE |
|---|---|---|---|
| 2 | 137 | 1916-1935 | MNRLIAFASRGNHVSPTHYV |
| 1 | 59 | 1921-1940 | AFASRGNHVSPTHYVPESDA |
| 3 | 138 | 1924-1943 | SRGNHVSPTHYVPESDAAAR |
| 4 | 139 | 1927-1946 | NHVSPTHYVPESDAAARVTA |

TABLE 2

REACTIVITY OF 10 aa SYNTHETIC PEPTIDES WITH ANTI-HCV POSITIVE SERA

| SEQ ID NO: | Peptide Sequence | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| 6 | MNRLIAFASR | | | | | | | | | | | | | | | | |
| 7 | IAFASRGNHV | | | | | | | | | | | | | | | | |
| 8 | AFASRGNHVS | | | | | | | | | | | | | | | | |
| 9 | FASRGNHVSPGG* | | | | | | | | | | | | | | | | |
| 10 | ASRGNNVSPTG* | | | | | | | | | | | | | | | | |
| 11 | SRGNHVSPTH | | E | | | F | | | | | B | | B | | | | |
| 12 | RGNHVSPTHY | C | F | C | A | F | | | | | F | F | D | | | | D |
| 13 | GNHVSPTHYV | D | F | C | C | F | | | | | E | F | D | A | | | D |
| 14 | NHVSPTHYVPGG* | F | F | D | B | F | | | | | E | F | D | | | | C |
| 15 | HVSPTHYVPE | D | F | D | A | F | B | | | | B | E | B | A | | | B |
| 16 | VSPTHYVPES | D | F | D | | D | A | | | | A | B | | A | | | |
| 17 | SPTHYVPESD | C | F | C | | E | B | | | | | C | | A | | | |
| 18 | PTHYVPESDA | | B | | | C | | | | | | | | | | | |
| 19 | THYVPRSDAA | | | | | | | | | | | | | | | | |
| 20 | HYVPESDAAA | | | | | | | | | | | | | | | | |
| 21 | YVPESDAAAR | | | | | | | | | | | | | | | | |
| 22 | VPESDAAARV | | | | | | | | | | | | | | | | |
| 23 | PESDAAARVT | | | | | | | | | | | | | | | | |
| 24 | SDAAARVTLS | | | | | | | | | | | | | | | | |

| SEQ. ID NO: | Peptide Sequence | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|
| 6 | MNRLIAFASR | | | | | | | | | | | | | | | | |
| 7 | IAFASRGNHV | | | | | | | | | | | | | | | | |
| 8 | AFASRGNHVS | | | | | | | | | | | | | | | | |
| 9 | FASRGNHVSPGG* | | | | | | | | | | | | | | | | |
| 10 | ASRGNNVSPTG* | | | | | | | | | | | | | | | | |
| 11 | SRGNHVSPTH | | F | B | | E | D | | E | | | | | | | | E |
| 12 | RGNHVSPTHY | D | B | E | F | D | F | D | | F | | | | | A | | F |
| 13 | GNHVSPTHYV | D | D | E | F | E | F | D | | F | | | | | D | | E |
| 14 | NHVSPTHYVPGG* | A | C | F | F | D | D | C | D | D | | B | | | A | | F |
| 15 | HVSPTHYVPE | B | E | F | F | C | C | C | | C | | E | | | A | | E |
| 16 | VSPTHYVPES | | | D | D | F | D | D | B | | A | | C | | A | | E |
| 17 | SPTHYVPESD | A | F | C | F | C | D | A | A | | | D | | | B | | E |
| 18 | PTHYVPESDA | A | C | | | | | | | | | | | A | | | |
| 19 | THYVPRSDAA | | | | | | | | | | | | | | | | |
| 20 | HYVPESDAAA | | | | | | | | | | | | | | | | |
| 21 | YVPESDAAAR | | | | | | | | | | | | | | | | |
| 22 | VPESDAAARV | | | | | | | | | | | | | | | | |

TABLE 2-continued

REACTIVITY OF 10 aa SYNTHETIC PEPTIDES WITH ANTI-HCV POSITIVE SERA

| | |
|---|---|
| 23 | PESDAAARVT |
| 24 | SDAAARVTLS |

*the C-terminal Gly—Gly or single Gly were artificially added and do not belong to HCV sequence
A - P/N = 5–10; B - P/N = 11–20; C - P/N = 21–30; D - P/N = 31–40; E - P/N = 41–50; F - P/N > 50

TABLE 3

REACTIVITY OF 6 aa SYNTHETIC PEPTIDES WITH ANTI-HCV POSITIVE SERA

| SEQ ID NO: | Peptide Sequence | Serum Specimens | | | | | | | | | | | | | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 |
| 25 | GGSRGNHVGG | | | | | | | | | | | | | | | | |
| 26 | GGRGNHVSGG | | | | | | | | | | | | | | | | |
| 27 | GGGNHVSPGG | | | | | | | | | | | | | | | | |
| 28 | GGNHVSPTGG | | | | | | | | | | | | | | | | |
| 29 | GGHVSPTHGG | A | D | A | | D | | | | | D | | C | | | | |
| 30 | GGVSPTHYGG | A | C | A | A | C | | | | | A | C | A | | | | C |
| 31 | GGSPTHYVGG | B | F | | C | D | | | | | A | D | A | | | | C |
| 32 | GGPTHYVPGG | B | C | C | C | C | | C | | | A | E | | | A | | |
| 33 | GGTHYVPEGG | A | | | A | D | | | | | | | | | | | |
| 34 | GGHYVPESGG | A | | | | D | | | | | | | | | | | |
| 35 | GGYVPESDGG | | | | | | | | | | | | | | | | |
| 36 | GGVPESDAGG | | | | | | | | | | | | | | | | |
| 37 | GGPESDAAGG | | | | | | | | | | | | | | | | |

| SEQ ID NO: | Peptide Sequence* | Serum Specimens | | | | | | | | | | | | | | | |
|---|---|---|---|---|---|---|---|---|---|---|---|---|---|---|---|---|---|
| | | 17 | 18 | 19 | 20 | 21 | 22 | 23 | 24 | 25 | 26 | 27 | 28 | 29 | 30 | 31 | 32 |
| 25 | GGSRGNHVGG | | | | | | | | | | | | | | | | |
| 26 | GGRGNHVSGG | | | | | | | | | | | | | | | | |
| 27 | GGGNHVSPGG | | | | | | | | | | | | | | | | |
| 28 | GGNHVSPTGG | | | | | | | | | | | | | | | | |
| 29 | GGHVSPTHGG | | | F | D | | C | D | | D | | | | | A | | D |
| 30 | GGVSPTHYGG | B | | F | E | A | B | B | | B | | | | | A | | C |
| 31 | GGSPTHYVGG | | B | F | E | B | D | | | | | | | | F | | F |
| 32 | GGPTHYVPGG | | | B | D | | | | E | | | C | | | D | | F |
| 33 | GGTHYVPEGG | | | | | | | | | | | | | | | | |
| 34 | GGHYVPESGG | | | | | | | | | | | | | | | | |
| 35 | GGYVPESDGG | | | | | | | | | | | | | | | | |
| 36 | GGVPESDAGG | | | | | | | | | | | | | | | | |
| 37 | GGPESDAAGG | | | | | | | | | | | | | | | | |

*the C-terminal Gly—Gly were artifically added during the chemical synthesis and do not belong to the HCV sequence
A - P/N = 5–10; B - P/N = 11–20; C - P/N = 21–30; D - P/N = 31–40; E - P/N = 41–50; F - P/N > 50

REFERENCES

1. Alter, M. J. 1991. Hepatitis C: a sleeping giant? Am. J. Med. 91, Suppl. 3B, 112S–115S.
2. Bradley, D. W., M. J. Beach, and M. A. Purdy. 1993. Molecular characterization of hepatitis C and E viruses. Arch. Virol. (Suppl.) 7, 1–14.
3. Cerino, A., and M. U. Mondelli. 1991. Identification of an immunodominant B cell epitope on the hepatitis C virus nonstructural region defined by human monoclonal antibodies. J. Immunol. 147, 2692–2696.
4. Chiba, J., H. Ohba, Y. Matsuura, Y. Watanabe, T. Katayama, S. Kikuchi, L. Saito, and T. Miyamura. 1991. Serodiagnosis of hepatitis C virus (HCV) infection with an HCV core protein molecularly expressed by a recombinant baculovirus. Proc. Natl. Acad. Sci. USA 88, 4641–4645.
5. Chien, D. Y., Q.-L. Choo, A. Tabrizi, C. Kuo, J. Mcfarland, K. Berger, C. Lee, J. R. Shuster, T. Nguyen, D. L Moyer, M. Tong, S. Furuta, M. Omata, G. Tegmeier, H. Alter, E. Schiff, L. Jeffers, M. Houghton, and G. Kuo. 1992. Diagnosis of hepatitis C virus (HCV) infection using an immunodominant chimeric polyprotein to capture circulating antibodies: reevaluation of the role of HCV in liver diseases. Proc. Natl. Acad. Sci. USA 89, 10011–10015.
6. Ching, W. M., C. Wychowski, M. J. Beach, H. Wang, C. L. Davies, M. Carl, D. W. Bradley, H. J. Alter, S. M. Feinstone, and J. W. Shih. 1992. Interaction of immune sera with synthetic peptides corresponding to the structural protein region of hepatitis C virus. Proc. Natl. Acad. Sci. USA 89, 3190–3194.
7. Choo, Q.-L., A. J. Weiner, L. R. Overby, G. Kuo, M. Houghton, and D. W. Bradley. 1990. Hepatitis C virus: the major causative agent of vital non-A, non-B hepatitis. Brit. Med. Bull. 46, 423–441.
8. Kuo, G., Q.-L. Choo, H. J. Alter, G. L. Gitnick, A. G. Redeker, R. H. Purcell, T. Miyamura, J. L Dienstag, M. J. Alter, C. E. Stevens, G. E. Tegmeiter, F. Bonino, M. Colombo, W.-S. Lee, C. Kuo, K. Berger, J. R. Shuster, L. R. Overby, D. W. Bradley, and Houghton, M. (1989). An assay for circulating antibodies to a major etiologic virus of human non-A, non-B hepatitis. Science 244, 362–364.
9. Muraiso, I. C., M. Hijikata, S. Ohkoshi, M. J. Cho, M. Kikuchi, N. Kato, and K. A. Shimotohno. 1990. A structural protein of hepatitis c virus expressed in *E. coli* facilitates accurate detection of hepatitis C virus. Biochem. Biophys. Res. Commun. 172, 511–516.
10. van der Poel, C. L., H. T. M. Cuypers, H. W. Reesink, A. J. Weiner, S. Quan, R. di Nello, J. J. P. van Boven, I. Winkel, D. Mulder-Folkerts, P. J. Exel-Oehlers, W. Schaasberg, A. Leentvaar-Kuypers, A. Polito, M. Houghton, and P. N. Lelie. 1991. Confirmation of hepatitis C virus infection by new four-antigen recombinant immunoblot assay. Lancet 337, 317–319.
11. Riezu-Boj, J. I., D. Parker, M. P. Civeira, D. Phippard, T. P. Corbishley, J. Camps, A. Castilla, and J. Prieto. 1992. Detection of hepatitis C virus antibodies with new recombinant antigens: assessment in chronic liver diseases. J. Hepatol. 15, 309–313.
12. Simmonds, P., K. A. Rose, S. Graham, S.-W. Chan, F. McOmish, B. C Dow, E. A. C. Follett, P. L. Yap, and H. Marsden. 1993. Mapping of serotype-specific, immunodominant epitopes in the NS4 region of hepatitis C virus (HCV): use of type-specific peptides to serologically differentiate infections with HCV types 1, 2, and 3. J. Clin. Microbiol. 31, 1493–1503.
13. Zaaijer, H. L., L. T. Mimms, H. T. M. Cuypers, H. W. Reesink, C. L. van der Poel, S. Taskar, and P. N. Lelie. 1993. Variability of IgM response in hepatitis C virus infection. J. Med. Virol. 40, 184–187.
14. Harlow and Lane, Antibodies: A Laboratory Manual, Cold Springs Harbor Laboratory, Cold Spring Harbor, N.Y. 1988.
15. Kelly et al., Bio/Technology 10:163–167, 1992.
16. Bebbington et al., Bio/Technology 10:169–175, 1992.
17. Nasoff, M. S., S. L. Zebedee, G. Inchauspe, and A. M. Prince. 1991. Identification of an immunodominant epitope within the capsid protein of hepatitis C virus. Proc. Nat. Acad. Sci. USA 88, 5462–5466.
18. Sallberg, M., U. Ruden, B. Wahren and L. O. Magnius. 1992. Immunodominant regions within the hepatitis C virus core and putative matrix proteins. J. Clin. Microb. 30, 1989–1994.
19. Berasain, C., M. Garcia-Granero, J. I. Riezu-Boj, M. P. Civeira, J. Prieto, and F. Borras-Cuesta. 1993. Detection of anti-hepatitis C virus antibodies by ELISA using synthetic peptides. J. Hepatol. 18, 80–84.
20. Hosein, B., C. T. Fang, M. A. Popovsky, J. Ye, M. Zhang, and C. Y. Wang. 1991. Improved serodiagnosis of hepatitis C virus infection with synthetic peptide antigen from capsid protein. Proc. Natl. Acad. Sci. USA 88, 3647–3651.
21. Barany, G., and R. B. Merrifield. 1980. Solid-phase peptide synthesis. In: The Peptides (E. Gross and J. Meienhofer, Eds.), Vol. 1, pp. 1–284. Academic Press, New York.
22. Arnon, R. (Ed.) Synthetic. Vaccines I:83–92, CRC Press, Inc., Boca Raton, Fla., 1987).
23. Inoue, Y., R. Suzuki, Y. Matsuura, S. Harada, J. Chiba, Y. Watanabe, I. Saito, and T. Miyamura. 1992. Expression of the amino-terminal half of the NS1 region of the hepatitis C virus genome and detection of an antibody to the expressed protein in patients with liver diseases. J. Gen Virol. 73, 2151–2154.

---

What is claimed is:

1. A peptide that binds selectively to an anti-hepatitis C virus antibody from a chronic or acute hepatitis C virus infection, wherein the peptide is selected from the group consisting of SEQ ID NO:1, SEQ ID NO:2, SEQ ID NO:3, and SEQ ID NO:4.

2. The peptide of claim 1, wherein the peptide consists of the amino acid sequence AFASRGNHVSPTHYVPESDA (SEQ ID NO:1) and binds with greater strength to an anti-hepatitis C virus antibody from an acute hepatitis C virus infection than to an anti-hepatitis C virus antibody from a chronic hepatitis C virus infection.

3. The peptide of claim 1, wherein the peptide consists of the amino acid sequence MNRLIAFASRGNHVSPTHYV (SEQ ID NO:2) and binds with greater strength to an anti-hepatitis C virus antibody from an acute hepatitis C virus infection than to an anti-hepatitis C virus antibody from a chronic hepatitis C virus infection.

4. The peptide of claim 1, wherein the peptide consists of the amino acid sequence SRGNHVSPTHYVPESDAAAR (SEQ ID NO:3) and binds with greater strength to an anti-hepatitis C virus antibody from an acute hepatitis C virus infection than to an anti-hepatitis C virus antibody from a chronic hepatitis C virus infection.

5. The peptide of claim 1, wherein the peptide consists of the amino acid sequence NHVSPTHYVPESDAAARVTA (SEQ ID NO:4) and binds with equal strength to an anti-hepatitis C virus antibody from an acute hepatitis C virus infection and an anti-hepatitis C virus antibody from a chronic hepatitis C virus infection.

6. A method of differentiating acute and chronic hepatitis C virus infection in a subject comprising:
  a) contacting an antibody-containing sample from the subject with one or more peptides selected from the group consisting of a peptide as defined in the Sequence Listing as SEQ ID NO:1, a peptide as defined in the Sequence Listing as SEQ ID NO:2 and a peptide as defined in the Sequence Listing as SEQ ID NO:3 under conditions that permit binding between the peptide and the antibodies;

b) detecting the presence of binding between the peptide and the antibodies in step a);

c) contacting the antibody-containing sample from the subject with an amount of a peptide as defined in the Sequence Listing as SEQ ID NO:4 under conditions that permit binding between the peptide and the antibodies;

d) detecting the presence of binding between the peptide and the antibodies in step c); and e) comparing the strength of the antibody binding of step b) with the strength of the antibody binding of step d), a stronger binding in step b) as compared to the binding in step d) indicating acute hepatitis C virus infection and an equivalent binding in both steps b) and d) indicating chronic hepatitis C virus infection.

7. The method of claim 6, wherein two peptides in step a) are contacted with the antibody-containing sample.

8. The method of claim 7, wherein each of two said peptides is contacted separately with the antibody-containing sample.

9. The method of claim 6, wherein all three peptides in step a) are contacted with the antibody-containing sample.

10. The method of claim 9, wherein each of said three peptides is contacted separately with the antibody-containing sample.

11. A method of diagnosing an acute hepatitis C virus infection in a subject comprising contacting an antibody-containing sample from the subject with one or more peptides selected from the group as defined in the Sequence Listing as SEQ ID NO:1, SEQ ID NO:2, and SEQ ID NO:3 and comparing the strength of binding between said one or more peptides and the antibodies from the sample with the strength of binding between the peptide defined in the Sequence Listing as SEQ ID NO:4 and the antibodies from the sample, wherein stronger binding between said one or more peptides of SEQ ID NO:1, SEQ ID NO:2, and SEQ ID NO:3 and said antibodies as compared to binding between the peptide defined in the Sequence Listing as SEQ ID NO:4 and said antibodies indicates an acute hepatitis C virus infection.

* * * * *